(12) United States Patent
Wu et al.

(10) Patent No.: US 11,091,736 B2
(45) Date of Patent: Aug. 17, 2021

(54) METHOD OF MICROBIAL ENHANCED OIL RECOVERY BY CHANGING MICROBIAL MOTILITY

(71) Applicant: PEKING UNIVERSITY, Beijing (CN)

(72) Inventors: Xiaolei Wu, Beijing (CN); Yong Nie, Beijing (CN); Miaoxiao Wang, Beijing (CN); Shuang Geng, Beijing (CN); Jianwei Wang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 0 days.

(21) Appl. No.: 16/999,725

(22) Filed: Aug. 21, 2020

(65) Prior Publication Data
US 2021/0054258 A1    Feb. 25, 2021

(30) Foreign Application Priority Data
Aug. 23, 2019 (CN) .......................... 201910782140.1

(51) Int. Cl.
| | | |
|---|---|---|
| *C12N 1/20* | (2006.01) | |
| *C09K 8/582* | (2006.01) | |
| *C12N 1/26* | (2006.01) | |
| *C12Q 1/02* | (2006.01) | |
| *E21B 43/20* | (2006.01) | |

(52) U.S. Cl.
CPC ................ *C12N 1/20* (2013.01); *C09K 8/582* (2013.01); *C12N 1/26* (2013.01); *C12Q 1/02* (2013.01); *E21B 43/20* (2013.01)

(58) Field of Classification Search
CPC . C09K 8/582; C12N 1/26; C12N 1/20; C12Q 1/02; C12Q 1/04; E21B 43/20; C12P 39/00
See application file for complete search history.

(56) References Cited

U.S. PATENT DOCUMENTS 10,202,620 B2    2/2019  Coelho et al.

FOREIGN PATENT DOCUMENTS

| CN | 102559165 A | 7/2012 |
|---|---|---|
| CN | 106226169 A | 12/2016 |
| CN | 107100601 A | 8/2017 |
| CN | 107558972 A | 1/2018 |

OTHER PUBLICATIONS

Geng, S et al. *Glycocaulis alkaliphilus* sp. nov., a dimorphic prosthecate bacterium isolated from crude oil. International Journal of Systematic and Evolutionary Microbiology. 2015. 65: 838-844. (Year: 2015).*
Liang, J et al. Regulationof alkane degradation pathway by a TetR family repressor via an autoregulation positive feedback mechanism in a Gram-positive Dietzia bacterium. 2016. 99(2): 338-359. (Year: 2016).*
Tittsler, RP et al. The use of semi-solid agar for the detection of bacterial motility. Journal of Bacteriology. 1936. 31(6): 575-580. (Year: 1936).*
Wang, M et al. Sessile bacterium unlocks ability of surface motility through mutualistic interspecies interaction. Environmental Microbiology Reports. 2021. 13(2): 112-118. (Year: 2021).*
Shuang Geng et al. *Glycocaulis alkaliphilus* sp. nov., a dimorphic prosthecate bacterium isolated from crude oil, Dec. 2014,No. 3,vol. 65, pp. 838-844.
Jie-Liang Liang, et al. Regulation of alkane degradation pathway by a TetR family repressor via an autoregulation positive feedback mechanism in a Gram-positive Dietzia bacterium, Jan. 2016,No. 2,vol. 99, pp. 338-359.
Xing-Biao Wang et al. Degradation of petroleum hydrocarbons (C6—C40) and crude oil by a novel Dietzia strain, Sep. 2011, No. 17, vol. 102, pp. 7755-7761.
Huang Zijun et al. Research and application of key technology for improving microbial enhanced oil recovery, Feb. 2018, No. 2, vol. 37, 5 pages.
Chen Wenxin et al. Microbial oil recovery technology and its foreign application research progress, Jul. 2009, No. 4, vol. 24.
Liu Yang et al. Effectsofcellsurface-Hydrophobicitieson Migration and Adhension of Oil Recovering Microbe,Oct. 2009, No. 5, vol. 31, pp. 117-120.
Jing Guicheng et al. Studies on the Chemotaxis of a Bacterium *Pseudomonas* sp. Using Crude Oil as Carbon Source, Mar. 2005, No. 2, vol. 22, pp. 187-190.

* cited by examiner

Primary Examiner — David W Berke-Schlessel
Assistant Examiner — Susan E. Fernandez

(57) ABSTRACT

Disclosed herein is a method of microbial enhanced oil recovery by changing microbial motility, including: subjecting a viable *Glycocaulis* strain and the alkane-degrading *Dietzia* strain to contact culture to enable the alkane-degrading *Dietzia* strain to have motility. This application also provides a method for microbial enhanced oil recovery, including: subjecting a viable *Glycocaulis* strain and the alkane-degrading *Dietzia* strain to contact culture to enable the alkane-degrading *Dietzia* strain to have motility; and injecting the contact culture mixture of the viable *Glycocaulis* strain and the alkane-degrading *Dietzia* strain to an oil well to perform microbial enhanced oil recovery.

3 Claims, 4 Drawing Sheets

METHOD OF MICROBIAL ENHANCED OIL RECOVERY BY CHANGING MICROBIAL MOTILITY

CROSS-REFERENCE TO RELATED APPLICATIONS

This application claims the benefit of priority from Chinese Patent Application No. 201910782140.1, filed on Aug. 23, 2019. The content of the aforementioned application, including any intervening amendments thereto, is incorporated herein by reference in its entirety.

TECHNICAL FIELD

This disclosure relates to biological technology, and more particularly to a method of microbial enhanced oil recovery by changing microbial motility.

BACKGROUND

Many oilfields in the later stage of production produces fluids with high water content, and the recoverable underground reserves has been shrinking. Moreover, the high water-cut reservoirs, oil-water transition zones and heavy oil reservoirs have exceeded the conventional crude oil in reserves. Considering the obvious deterioration in the quality of the crude oil and the difficulties in the exploitation, it is urgently required to develop a novel oil recovery method.

Microbial enhanced oil recovery (MEOR) has received worldwide attention due to the advantages of wide application, simple operation, low cost, long acting time and green process. In the MEOR, the microorganisms, based on their biodegrading properties and metabolites, play a significant role in lowering the viscosity and freezing point of crude oil to further improve the fluidity, enhancing the production and recovery of crude oil. Therefore, a desired target microorganism used in the MEOR is required to have rapid proliferation, good motility, high resistance to stress and excellent degradation ability.

However, many species of microorganisms employed in the MEOR are lack of motility, so they fail to migrate freely to fully contact with crude oil in the reservoir, failing to effectively enhance the oil recovery. Surface motility refers to the ability of a microorganism to migrate on a solid surface. A good surface motility enables the microorganisms to migrate along the rock surface into an operation blind area where it is difficult to enter through other oil recovery techniques, so it is conducive to the enlargement of oil displacement range and the enhancement of the crude oil recovery, improving the recovery rate of crude oil.

SUMMARY

In order to change the motility of microorganisms for oil recovery to further improve the microbial enhanced oil recovery and promote the recovery rate of crude oil, this application provides a method of microbial enhanced oil recovery by changing microbial motility.

The technical solutions of this application are specifically described as follows.

In a first aspect, this application provides a method of changing a motility of an alkane-degrading *Dietzia* strain, comprising:

subjecting a viable *Glycocaulis* strain and the alkane-degrading *Dietzia* strain to contact culture to enable the alkane-degrading *Dietzia* strain to have motility.

In an embodiment, the change of the motility of the alkane-degrading *Dietzia* strain is to improve the surface motility of the alkane-degrading *Dietzia* strain.

In an embodiment, the viable *Glycocaulis* strain is viable *Glycocaulis* sp. 6B-8; and the alkane-degrading *Dietzia* strain is *Dietzia* sp. DQ12-45-1b.

In a second aspect, this application provides a microbial enhanced oil recovery method, comprising:

subjecting a viable *Glycocaulis* strain and the alkane-degrading *Dietzia* strain to contact culture to enable the alkane-degrading *Dietzia* strain to have motility; and injecting the contact culture mixture of the viable *Glycocaulis* strain and the alkane-degrading *Dietzia* strain to an oil well to perform microbial enhanced oil recovery.

In an embodiment, the viable *Glycocaulis* strain is viable *Glycocaulis* sp. 6B-8; and the alkane-degrading *Dietzia* strain is *Dietzia* sp. DQ12-45-1b.

In a third aspect, this application provides a composition for microbial enhanced oil recovery, comprising:

alkane-degrading *Dietzia* sp. DQ12-45-1b;
*Glycocaulis* sp. 6B-8; and
a culture medium for contact culture of *Dietzia* sp. DQ12-45-1b and *Glycocaulis* sp. 6B-8.

In an embodiment, the enhancement of the microbial oil recovery is to improve the recovery rate of the microbial oil recovery.

Compared to the prior art, the invention has the following beneficial effects.

The surface motility of the alkane-degrading *Dietzia* strain can be improved by contact co-culture with the viable *Glycocaulis* strain, thus improving the microbial enhanced oil recovery.

BRIEF DESCRIPTION OF THE DRAWINGS

FIG. 1A: *Dietzia* sp. DQ12-45-1b; FIG. 1B: *Glycocaulis* sp. 6B-8; FIG. 1C: *Dietzia* sp. DQ12-45-1b with viable *Glycocaulis* sp. 6B-8 cells; and FIG. 1D: *Dietzia* sp. DQ12-45-1b with dead *Glycocaulis* sp. 6B-8 cells.

DETAILED DESCRIPTION OF EMBODIMENTS

Figure 1A:
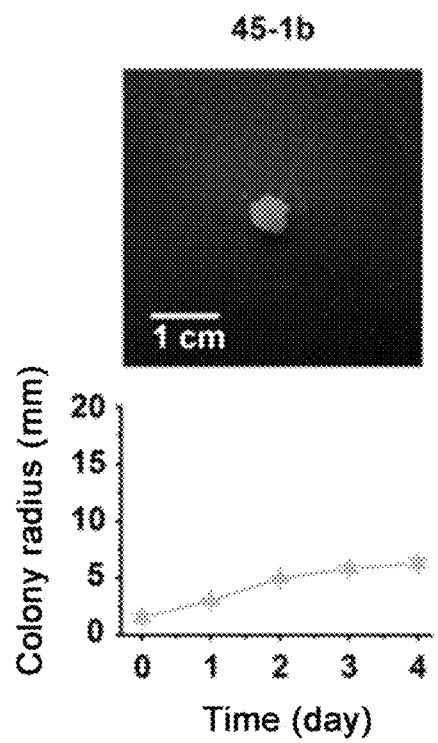
FIGS. 1A-D illustrates the change of colony radius of *Dietzia* sp. DQ12-45-1b and *Glycocaulis* sp. 6B-8 over time.

Unless otherwise specified, the experimental methods employed in the following embodiments are conventional methods.

Unless otherwise specified, the materials and reagents used in the following embodiments are all commercially available.

Example 1

Alkane-degrading *Dietzia* sp. DQ12-45-1b and *Glycocaulis* sp. 6B-8 isolated from Daqing oilfield were selected herein as research objects, where *Dietzia* sp. DQ12-45-1b had been specifically described in "Detection of Metabolites from n-Hexadecane Degradation by Strain *Dietzia* sp. DQ12-45-1b", and *Glycocaulis* sp. 6B-8 had been recorded in "*Glycocaulis alkaliphilus* sp. nov., a dimorphic prosthecate bacterium isolated from crude oil" (abbreviated as 6B-8).

1. Investigation on Motility of *Dietzia* sp. DQ12-45-1b and *Glycocaulis* sp. 6B-8

1.1 Preparation of *Dietzia* sp. DQ12-45-1b and *Glycocaulis* sp. 6B-8 Suspensions (1) Preparation of *Dietzia* sp. DQ12-45-1b Suspension The strain *Dietzia* sp. DQ12-45-1b was transferred from a glycerol tube to a plate for activation, and the monoclonal cells were picked and transferred to a test tube containing liquid medium for culture. Then the bacterial suspension in the test tube was transferred to a 500 mL Erlenmeyer flask containing 300 mL of glucose-peptone-yeast extract (GPY) medium and cultured to obtain a seed solution, where the GPY medium (1 L) consisted of 10 g of peptone, 5 g of yeast extract, 10 g of glucose and water, and was adjusted to pH 8.0.

After cultured to the logarithmic growth phase, the seed solution was centrifuged at 5,000 rpm and 4° C. for 10 min, and the cells were collected, washed twice with a MF medium and suspended with the MF medium to a density of $1 \times 10^7$ cells/mL to produce the *Dietzia* sp. DQ12-45-1b suspension, where the MF medium (1 L) consisted of 17.9 g of $Na_2HPO_4.12H_2O$, 7.8 g of $NaH_2PO_4$, 5 g of $(NH_4)_2SO_4$, 5 g of KCl, 10 mL of a microelement solution SL-4 (A304-01, Shanghai Linyuan Biotechnology Co., Ltd), 1 mL of sterile 5% $CaCl_2$) solution, 1 mL of sterile $MgSO_4$ solution and water, and was adjusted to pH 8.0.

Glucose-peptone-yeast extract (GPY) medium (1 L) was prepared from 10 g of peptone, 5 g of yeast extract, 10 g of glucose and water, and was adjusted to pH 8.0.

(2) Preparation of *Glycocaulis* sp. 6B-8 Suspension

The *Glycocaulis* sp. 6B-8 suspension with a density of $1 \times 10^7$ cells/mL was prepared according to the above preparation of the *Dietzia* sp. DQ12-45-1b suspension.

1.2 Investigation of Bacterial Motility

Due to the failure in utilizing alkane and glucose as carbon sources to grow, *Glycocaulis* sp. 6B-8 was culture in a LB medium.

Three groups of experiments were designed.

Group 1 Measurement of Surface Motility of Single Strain

A drop of the *Dietzia* sp. DQ12-45-1b suspension was spotted on a MF plate containing 0.5% agar with 0.5% hexadecane as the sole carbon source, and the surface motility was measured 24 h later, where a cover of the plate was added with a filter paper adsorbing 0.5% of hexadecane (the size of the filter paper was the same as that of the plate with a diameter of 90 mm) for inverted culture.

A drop of the *Glycocaulis* sp. 6B-8 suspension was spotted on a LB plate containing 0.5% of agar, and the surface motility was measured 24 h later.

Group 2 Surface Motility of *Dietzia* sp. DQ12-45-1b Under Co-Culture with Viable *Glycocaulis* sp. 6B-8 Cells The *Glycocaulis* sp. 6B-8 suspension and a solid MF medium (containing 5 g agar per liter of a liquid MF medium) were blended evenly at 55° C. and cooled to form a plate. Then a drop of the *Dietzia* sp. DQ12-45-1b suspension was spotted on the plate, and a cover of the plate was added with a filter paper adsorbing 1 mL of hexadecane (the size of the filter paper was the same as that of the plate with a diameter of 90 mm) for culture.

Group 3 Surface Motility of *Dietzia* sp. DQ12-45-1b Under Co-Culture with Dead *Glycocaulis* sp. 6B-8 Cells The *Glycocaulis* sp. 6B-8 suspension was inactivated at high temperature.

The inactivated *Glycocaulis* sp. 6B-8 suspension and a solid MF medium containing 0.5% agar were blended at 55° C. and cooled to form a plate. A drop of the *Dietzia* sp. DQ12-45-1b suspension was spotted on the plate, and the plate was added with a filter paper adsorbing hexadecane at its cover and then cultured invertedly.

The plates in the above three groups were cultured for 24 h and then observed for the growth status (colony size) and motility (colonial diffusion size) of each strain.

The motion rate was calculated through dividing the diffusion radius by the growth time.

Figure 1B:
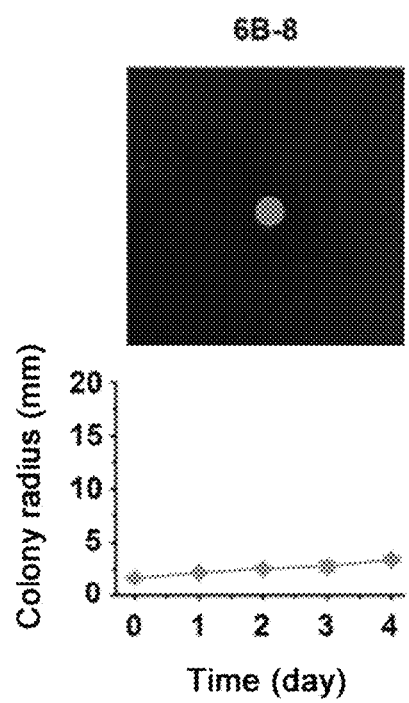
Figure 1C:
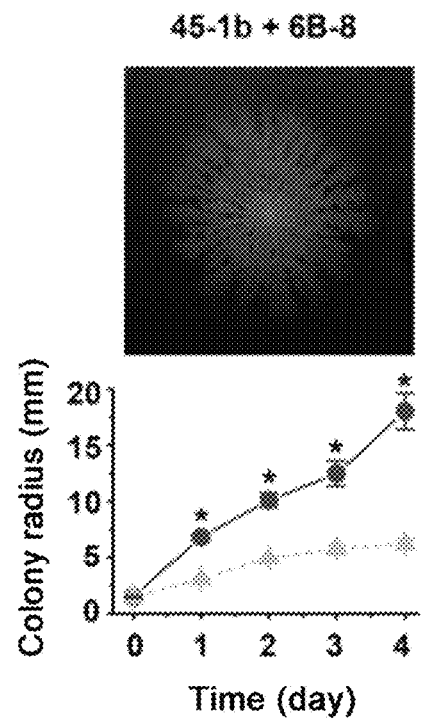

The results were shown in FIGS. 1A-D, where FIG. 1A: *Dietzia* sp. DQ12-45-1b; FIG. 1B: *Glycocaulis* sp. 6B-8; FIG. 1C: *Dietzia* sp. DQ12-45-1b with viable *Glycocaulis* sp. 6B-8 cells; and FIG. 1D: *Dietzia* sp. DQ12-45-1b with dead *Glycocaulis* sp. 6B-8 cells. In each of FIGS. 1A-D, the upper picture illustrated the colonial growth status, and the lower graph showed the change of colony radius over time.

Figure 1D:
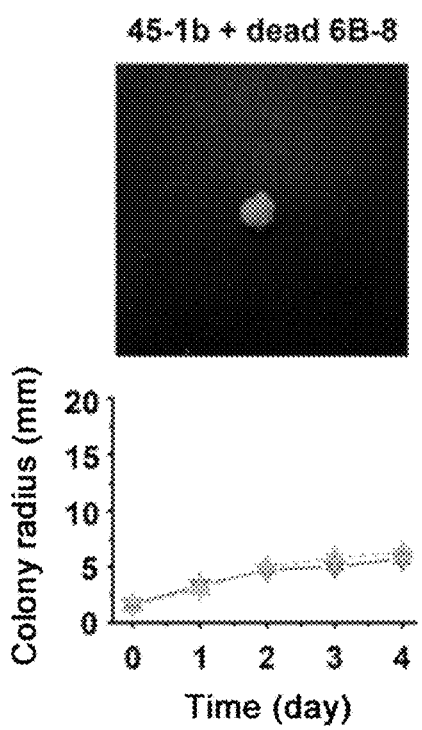

These figures clearly demonstrated that neither *Dietzia* sp. DQ12-45-1b nor *Glycocaulis* sp. 6B-8 exhibited surface motility when cultured individually (FIGS. 1A-B); when co-cultured with viable *Glycocaulis* sp. 6B-8 cells, *Dietzia* sp. DQ12-45-1b showed surface motility, and the colony diffused at a rate of 2.87±0.28 µm/min (FIG. 1C); while co-cultured with dead *Glycocaulis* sp. 6B-8 cells, *Dietzia* sp. DQ12-45-1b failed to show surface motility (FIG. 1D).

It can be concluded based on the above results that the presence of viable *Glycocaulis* sp. 6B-8 cells induced the occurrence of surface motility in *Dietzia* sp. DQ12-45-1b.

1.3 Investigation on Interaction Between *Dietzia* sp. DQ12-45-1b and *Glycocaulis* sp. 6B-8

Two experimental models, respectively non-contact culture and contact culture, were designed herein.

Non-Contact Culture

A drop of the *Glycocaulis* sp. 6B-8 suspension and a drop of the *Dietzia* sp. DQ12-45-1b were spotted on a solid MF medium (containing 0.5% agar with hexadecane as the sole carbon source) respectively at a distance of 0 cm (indicating that the two drops of suspensions were close to each other, and were separated merely by a microporous membrane), 1 cm and 2 cm. A solid MF medium only spotted with the *Dietzia* sp. DQ12-45-1b was used as control. A microporous membrane was provided between the two spots to prevent the two kinds of microorganisms from contacting with each other, but the metabolites were allowed to pass through the membrane (the bacterial cells were larger than the pore size (0.22 µm) of the microporous membrane, so they fail to pass through the membrane, but the metabolites were so small in size that they can pass through the membrane).

Contact Culture

A drop of the *Glycocaulis* sp. 6B-8 suspension and a drop of the *Dietzia* sp. DQ12-45-1b were spotted on a solid MF medium (containing 0.5% agar with hexadecane as the sole carbon source), where the two spots were close to each other.

After cultured for 24 h, the two strains in the non-contact culture and contact groups were measured for the growth status (colony size) and motility (colonial diffusion size).

Figure 3:
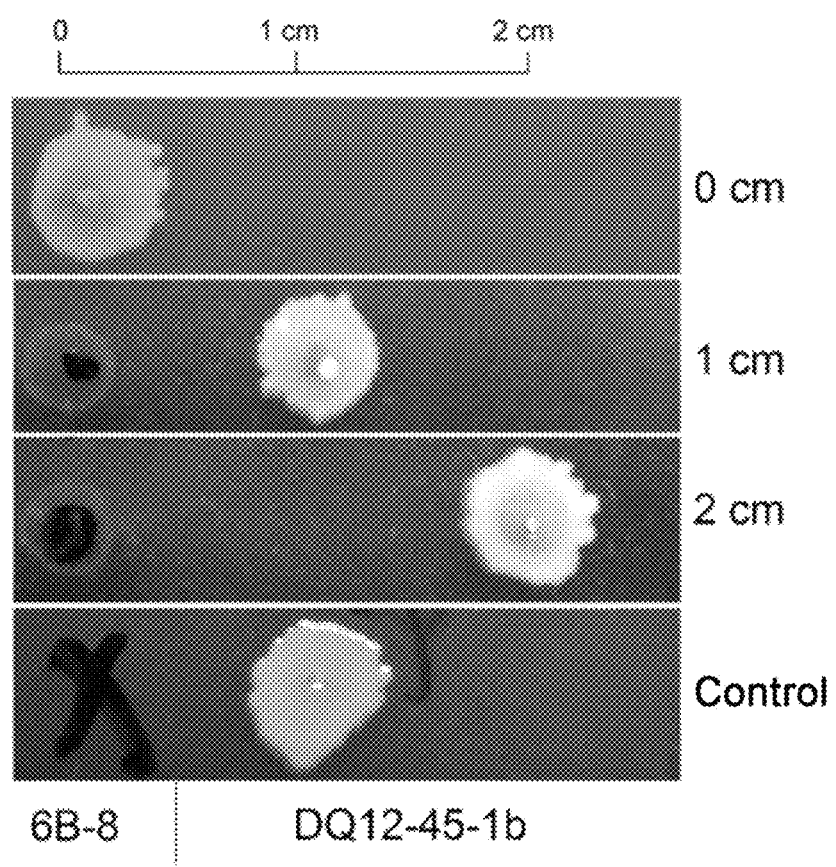
FIG. 3 shows the non-contact culture results of a *Glycocaulis* sp. 6B-8 suspension and a *Dietzia* sp. DQ12-45-1b suspension.

It can be seen from FIG. 3 that the two strains of bacteria both can grow in the MF medium, but neither of them exhibited surface motility, which indicated that the non-contact culture failed to cause *Dietzia* sp. DQ12-45-1b to show motility.

The results of the contact culture group were similar to those shown in FIG. 1C, specifically, the two strains of bacteria both can grow in the MF medium, and *Dietzia* sp.

DQ12-45-1b exhibited motility under the contact with viable *Glycocaulis* sp. 6B-8 cells, which indicated that the contact culture with the viable *Glycocaulis* sp. 6B-8 cells enabled the *Dietzia* sp. DQ12-45-1b to show motility.

Figure 2:
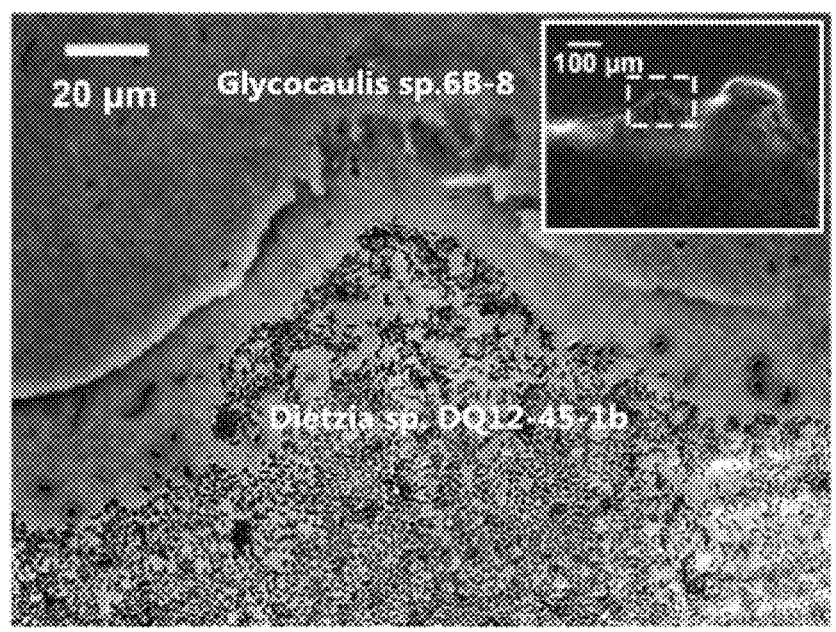
FIG. 2 shows the real-time observation results of the contact culture of *Dietzia* sp. DQ12-45-1b and *Glycocaulis* sp. 6B-8 using an electron microscope.

The microorganisms in the contact culture group were observed in real time under an electron microscope, and the results were shown in FIG. 2. It was surprisingly found that under contact with the viable *Glycocaulis* sp. 6B-8 cells, the capsule structure of the alkane-degrading strain *Dietzia* sp. DQ12-45-1b was broken by the *Glycocaulis* sp. 6B-8, resulting in the occurrence of a typical darting-motion surface motility in the alkane-degrading strain.

The darting-motion surface motility is a special surface motility, which was derived from the change in bacterial structure caused by the contact of two kinds of bacteria.

2. Investigation on the Darting-Motion Surface Motility of Alkane-Degrading Bacteria Caused by *Glycocaulis* Strains The investigation on the darting-motion surface motility of alkane-degrading bacteria caused by *Glycocaulis* strains was performed as follows.

A *Glycocaulis* bacterial suspension and a solid MF medium (containing 5 g of agar per liter of a liquid MF medium) were blended evenly at 55° C. and cooled to form a plate, onto which a drop of the alkane-degrading bacterial suspension was dripped. A cover of the plate was added with a filter paper adsorbing 1 mL of hexadecane, and the plate was cultured invertedly.

In order to further demonstrate the darting-motion surface motility of the alkane-degrading bacteria caused by the *Glycocaulis* strains, the following experiments were conducted.

1. Suspensions of *Glycocaulis abyssi* MCS33$^T$, *Glycocaulis albus* SLG210-30A1$^T$, *Glycocaulis* sp. 6B-8 and *Escherichia coli* DH5a were individually blended evenly with a solid MF medium (containing 5 g of agar per liter of a liquid MF medium) at 55° C. and cooled to form a solid plate. Each solid plate was dripped with a drop of the *Dietzia* sp. DQ12-45-1b suspension, and then cultured invertedly with the cover added with a filter paper adsorbing hexadecane.

A solid MF medium (0.5% agar) spotted with a drop of the *Dietzia* sp. DQ12-45-1b suspension was used as control.

2. The *Glycocaulis* sp. 6B-8 suspension and a solid MF medium (containing 5 g of agar per liter of a liquid MF medium) were blended uniformly at 55° C. and cooled to form a solid plate, which was then spotted with a drop of a *Dietzia* sp. DQ12-45-1b suspension, a *Dietzia* psychralcaliphila ILA-1$^T$ suspension and a *Dietzia timorensis* DSM 45568$^T$ suspension, respectively, and cultured invertedly with the cover added with a filter paper adsorbing hexadecane. The plates free of *Glycocaulis* sp. 6B-8 were individually spotted with the *Dietzia* suspensions and used as control.

The above-mentioned *Glycocaulis* strains (i.e., *Glycocaulis abyssi* MCS33$^T$, *Glycocaulis albus* SLG210-30A1$^T$ and *Glycocaulis* sp. 6B-8) had been described in Xiang-Lin L, Bai-Sheng X, Man C, et al. (*Glycocaulis albus* sp. nov. A moderately halophilic dimorphic prosthecate bacterium isolated from petroleum-contaminated saline soil [J]. *International Journal of Systematic and Evolutionary Microbiology*, 2014, 64(Pt 9)).

The alkane-degrading strain *Dietzia psychralcaliphila* ILA-1$^T$ had been mentioned in Yumoto I, Nakamura A, Iwata H, et al. (*Dietzia psychralcaliphila* sp. nov. a novel, facultatively psychrophilic alkaliphile that grows on hydrocarbons [J]. *International Journal of Systematic &Evolutionary Microbiology*, 2002, 52(Pt1):85). The alkane-degrading strain *Dietzia timorensis* DSM 45568$^T$ had been mentioned in Bell M E, Bernard K A, Harrington S M, et al. (*Lawsonella clevelandensis* gen. nov., sp. nov., a new member of the suborder Corynebacterineae isolated from human abscesses[J]. *International Journal of Systematic and Evolutionary Microbiology*, 2016, 66(8)).

Figure 4A:
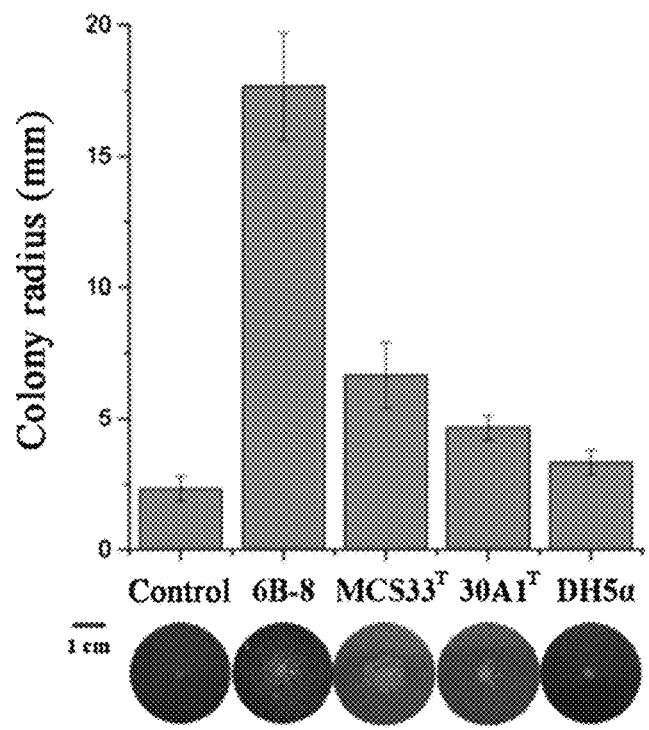
FIG. 4A shows the effect of various *Glycocaulis* strains on the surface motility of alkane-degrading *Dietzia* sp. DQ12-45-1b.
Figure 4B:
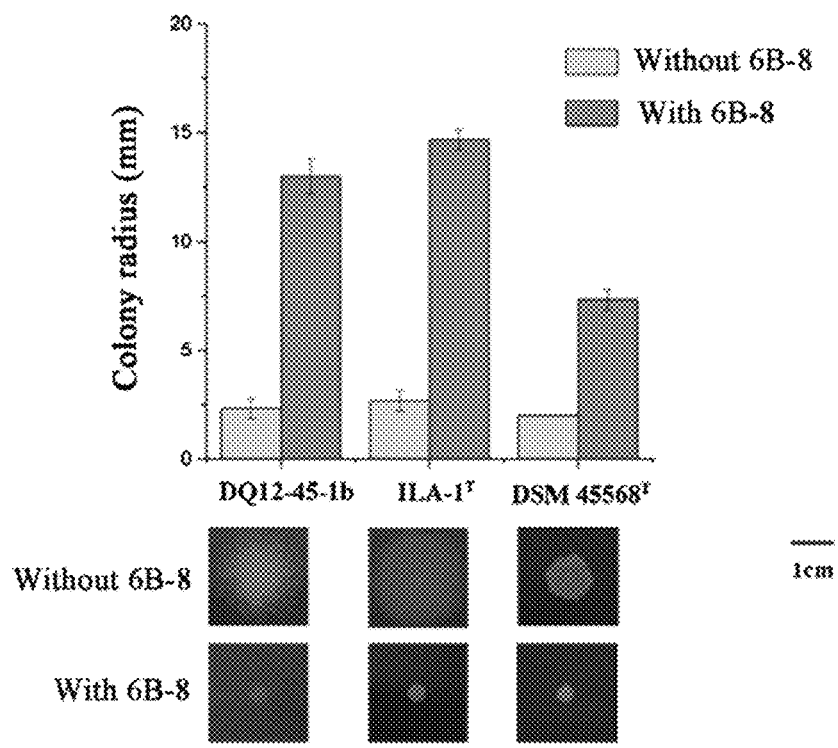
FIG. 4B shows the effect of *Glycocaulis* sp. 6B-8 on various alkane-degrading bacteria.

The growth status and motility of the *Dietzia* strains were detected, and the results were shown in FIGS. 4A-B.

It can be seen from FIG. 4A that the *Glycocaulis* strains *Glycocaulis* sp. 6B-8, *Glycocaulis abyssi* MCS33$^T$ and *Glycocaulis albus* SLG210-30A1$^T$ all enabled the alkane-degrading strain *Dietzia* sp. DQ12-45-1b to exhibit surface motility, and the alkane-degrading strain *Dietzia* sp. DQ12-45-1b did not show surface motility in the presence of the non-*Glycocaulis* strain *Escherichia coli* DH5α.

As shown in FIG. 4B, the alkane-degrading strains *Dietzia psychralcaliphila* ILA-1$^T$, *Dietzia timorensis* DSM 45568$^T$ and *Dietzia* sp. DQ12-45-1b all showed surface motility in the presence of the *Glycocaulis* strain *Glycocaulis* sp. 6B-8.

It can be concluded from the above that the *Glycocaulis* strains enabled the alkane-degrading bacterium to display the surface motility through the interaction therebetween. Therefore, a *Glycocaulis* strain and an alkane-degrading strain can be employed together in the microbial enhanced oil recovery to expand the microbial migration range and expose more residual oil to the microorganisms, enhancing the microbial oil recovery.

Example 2 Interaction Between a *Glycocaulis* Strain and an Alkane-Degrading Bacterium in Simulation Experiment A physical model experiment for enhancing the recovery rate for a natural core was conducted. The natural core had a porosity of 22.6%, a pore volume of 23.8 cm$^3$ and a water phase permeability of 178×10$^{-3}$ μm$^2$.

The water for injection was added with 1 g/L NH$_4$H$_2$PO$_4$, 1 g/L (NH$_4$)$_2$SO$_4$, 1 g/L K$_2$HPO$_4$, 1.2 g/L KNO$_3$, 0.5 g/L peptone and 0.5 g/L yeast extract, and the water for injection was 0.6 times the volume of the natural core.

Three experimental groups (Groups A, B and C) and one control group (Group D) were designed, where group A was added with 1 mL of the *Dietzia* sp. DQ12-45-1b suspension (10$^7$ cells/mL); group B was added with 1 mL of the *Glycocaulis* sp. 6B-8 suspension (10$^7$ cells/mL); group C was added with 0.5 mL of the *Dietzia* sp. DQ12-45-1b suspension (10$^7$ cells/mL) and 0.5 mL of the *Glycocaulis* sp. 6B-8 suspension (10$^7$ cells/mL); and group D was without any addition of bacterial suspension.

After cultured statically for 18 h, the core was sliced at an interval of 0.5 cm and washed with sterile water, and the water was collected and spread on a plate. The plate was cultured for 36 h and then observed for the motion of microorganisms.

The results were shown in Table 1, and it can be obtained that the microorganisms in group C, in which 0.5 mL of the *Dietzia* sp. DQ12-45-1b suspension (10$^7$ cells/mL) and 0.5 mL of the *Glycocaulis* sp. 6B-8 suspension (10$^7$ cells/mL) were added, showed a significantly larger motion distance, indicating that the *Glycocaulis* strain *Glycocaulis* sp. 6B-8 enabled the alkane-degrading strain *Dietzia* sp. DQ12-45-1b to exhibit the motility.

TABLE 1

| Motility test | |
|---|---|
| Group | Motion distance (cm) |
| A | 0.5 |
| B | 0.5 |
| C | 8.0 |
| D | 0 |

What is claimed is:

1. A method of changing a motility of an alkane-degrading *Dietzia* strain, comprising:
    subjecting a viable *Glycocaulis* strain and an alkane-degrading *Dietzia* strain to contact culture to enable the alkane-degrading *Dietzia* strain to have motility, wherein the viable *Glycocaulis* strain is viable *Glycocaulis* sp. 6B-8.

2. The method of claim 1, wherein the alkane-degrading *Dietzia* strain is *Dietzia* sp. DQ12-45-1b.

3. A method for microbial enhanced oil recovery, comprising:
    subjecting a viable *Glycocaulis* strain and an alkane-degrading *Dietzia* strain to contact culture to enable the alkane-degrading *Dietzia* strain to have motility; and
    injecting the contact culture mixture of the viable *Glycocaulis* strain and the alkane-degrading *Dietzia* strain to an oil well to perform microbial enhanced oil recovery;
    wherein the viable *Glycocaulis* strain is viable *Glycocaulis* sp. 6B-8; and the alkane-degrading *Dietzia* strain is *Dietzia* sp. DQ12-45-1b.

* * * * *